US009640287B2

(12) United States Patent
Lemer (10) Patent No.: US 9,640,287 B2
(45) Date of Patent: May 2, 2017

(54) SCREEN MADE OF RADIATION SHIELDING MATERIAL FOR PROTECTING AN OPERATOR FROM IONISING RADIATION (71) Applicant: LEMER PROTECTION ANTI-X PAR ABREVIATION SOCIETE LEMER PAX, Carquefou (FR)

(72) Inventor: Pierre-Marie Lemer, Nantes (FR)

(73) Assignee: LEMER PROTECTION ANTI-X PAR ABREVIATION SOCIETE LEMER PAX, Carquefou (FR)

( * ) Notice: Subject to any disclaimer, the term of this patent is extended or adjusted under 35 U.S.C. 154(b) by 0 days.

(21) Appl. No.: 14/416,886

(22) PCT Filed: Jul. 23, 2013

(86) PCT No.: PCT/FR2013/051778
§ 371 (c)(1),
(2) Date: Jan. 23, 2015

(87) PCT Pub. No.: WO2014/016513
PCT Pub. Date: Jan. 30, 2014

(65) Prior Publication Data
US 2015/0206609 A1    Jul. 23, 2015

(30) Foreign Application Priority Data

Jul. 24, 2012    (FR) ..................... 12 57176

(51) Int. Cl.
*G21F 5/00*    (2006.01)
*G21F 1/12*    (2006.01)
(Continued)

(52) U.S. Cl.
CPC .............. *G21F 1/125* (2013.01); *A61B 6/107* (2013.01); *A61B 50/13* (2016.02); *A61B 6/501* (2013.01); *A61B 6/504* (2013.01)

(58) Field of Classification Search
None
See application file for complete search history.

(56) References Cited

U.S. PATENT DOCUMENTS 3,308,297 A * 3/1967 Mansker ................ A61B 6/107
250/515.1
2006/0076522 A1 * 4/2006 Goldstein .............. A61B 6/107
250/515.1
(Continued)

FOREIGN PATENT DOCUMENTS

FR          2 915 868 A1    11/2008
FR    WO 2009156660 A2 * 12/2009    ............. A61B 6/107
(Continued)

OTHER PUBLICATIONS

International Search Report, dated Nov. 7, 2013, from corresponding PCT application.

*Primary Examiner* — Andrew Smyth
(74) *Attorney, Agent, or Firm* — Young & Thompson (57) ABSTRACT

A screen made of radiation shielding material for protecting an operator from ionizing radiation, includes: (i) a lower part equipped with a front wall made of radiation shielding material, having an upper border; (ii) an upper part equipped with a front wall made of a radiation shielding material, at least one part of which is transparent, which front wall includes a lower border; and (iii) at least one passage for the arms of the operator. The front walls of the upper part and of the lower part are separable from each other, the upper part being borne by supporting elements allowing the screen to be reversibly maneuvered either into an active radiation shielding position in which the upper and lower borders are juxtaposed, or into a retracted position in which the upper and lower borders are separated from each other, in order to free a space above the lower part.

14 Claims, 8 Drawing Sheets

(51) Int. Cl.
*A61B 6/10* (2006.01)
*A61B 50/13* (2016.01)
*A61B 6/00* (2006.01)

(56) References Cited

U.S. PATENT DOCUMENTS

| | | | |
|---|---|---|---|
| 2008/0217564 A1* | 9/2008 | Beyar | A61B 6/00 250/515.1 |
| 2009/0041190 A1* | 2/2009 | Laupper | A61B 5/4872 378/97 |
| 2010/0286752 A1* | 11/2010 | Hirata | A61N 5/0613 607/100 |
| 2010/0304060 A1* | 12/2010 | Lemer | A61B 6/107 428/34.1 |
| 2012/0049093 A1* | 3/2012 | Costea | A61B 6/107 250/515.1 |

FOREIGN PATENT DOCUMENTS

| | | | | |
|---|---|---|---|---|
| FR | WO 2009156660 A3 * | 2/2010 | | A61B 6/107 |
| WO | 2009/156660 A2 | 12/2009 | | |

* cited by examiner

SCREEN MADE OF RADIATION SHIELDING MATERIAL FOR PROTECTING AN OPERATOR FROM IONISING RADIATION

BACKGROUND OF THE INVENTION

Field of the Invention

The present invention relates to the radioprotective screens, and more particularly the screens that are used in medical environment or other, to protect an operator from emissions of ionising radiations, for example X-rays. It also relates to an equipment in the form of a sterile cover for covering such screens, with a view to using them in a sterile protected environment.

Description of the Related Art

Within the framework of some examinations or interventions, the patients are subjected to ionising radiations, in particular of the X-ray type, used for the purpose of control, diagnosis or treatment.

This is the case in particular for interventions such as catheterism, installation of pacemaker, vascular, neurological or urological examinations, CRM (Cardiac Rhythm Management), CRT (Cardiac Resynchronization Therapy) . . . .

It is then important to correctly protect the operator (technician, doctor, surgeon or other) from such radiations, on pain of exposing him/her to significant doses, cumulated over time, liable to generate various pathologies (necroses of the upper limbs, cerebral tumors, etc.).

Protection structures exist, which consist in clothes such as overalls, chasubles or aprons made of a radioprotective material, but that do not always cover the totality of the body and whose significant weight harms the comfort of the operator, limits his/her capacities of movement and generates a rapid fatigue.

Shields or screens also exist, which are consisted of panels or assemblies of panels made of a suitable radioprotective material, put directly on the ground or through a support base, for example a rolling frame.

For example, the document US20120049093 describes a screen structure, a vertical part of which is intended to come in position under a support table adapted for receiving a patient, and another vertical part of which, carried by the first one, is intended to come in position above said support table and the patient.

This second part is mounted vertically mobile relative to the first one, in particular to facilitate the positioning of the screen the nearest possible of the body of the patient lying on the table.

But such a structure is not adapted to allow an operator located on the protected side of the screen to accede, by his/her arms and hands, to the other side of this screen, for example to intervene on a part of the patient's body exposed to the radiations.

Other known radioprotective shields or screens, as described for example in the documents FR2915868, WO-2009/156660 or U.S. Pat. No. 3,308,297, consist in structures well adapted to protect an operator intervening on a patient exposed to radiations, through orifice(s) or opening(s) for the passage of his/her arms and hands.

But the current structures of this type do not always allow the operator to work in optimum conditions.

In particular, some interventions include intermediate phases or steps during which the operator does not need radioprotection, but needs a great freedom of movement, for example for the installation of implantable cardiac devices, pacemakers, defibrillators, etc.

The presence of the screen is then relatively embarrassing. The operator has to bypass it or the screen has to be temporarily moved apart, which is not easy to implement and poses problems of space, organisation and even of security within the intervention room.

SUMMARY OF THE INVENTION

The object of the present invention is to propose a new structure of radioprotective screen through which an intervener can pass his/her hands, and possibly his/her arms, to intervene on a patient, while having the remaining of his/her body efficiently protected from the radiations, this screen structure being adapted to be very easily conformed according to an optimum radioprotection configuration, but also according to a configuration in which the operator has a more significant freedom of movement, in particular as regards his/her upper limbs, for the access to the patient or to the close environment of the latter.

The radioprotective material screen according to the invention is hence of the type comprising:

a lower part that has a base and at least one front wall made of a radioprotective material, which front wall extends in a vertical or substantially vertical plane and has an upper edge, a front face and a rear face, an upper part having at least one front wall made of a radioprotective material, at least one part of which is transparent to permit a visual access through it, which front wall has a front face, a rear face and a lower edge, and at least one passage for the operator's arms, so that the latter can intervene on the non-radioprotected side, with the remaining of his/her body efficiently protected, said front wall of the lower part and said front wall of the upper part being arranged in the continuation of each other, by juxtaposition of their respective upper and lower edges, hence occupying an active position ensuring the desired protection.

And within the framework of the present invention, said front walls of the upper part and of the lower part are separable from each other, said upper part being carried by support means allowing the reversible operation thereof to a retracted position in which the lower edge of the front wall of the upper part is spaced apart from the upper edge of the front wall of the lower part, to clear a space above said lower part.

According to another characteristic, said passage for the operator's arms is arranged at the level of the zone of juxtaposition between said lower and upper parts, when these latter are in an active juxtaposed position.

In this case, said passage for the operator's arms is advantageously arranged at the level of the lower edge of the front wall of the upper part, and consists in a flexible curtain in the form of a plurality of vertical strips or bands juxtaposed to each other, made of a radioprotective material, and the upper end of which is fixed on an upper panel made of a radioprotective material.

According to another feature, the upper part of the screen is carried by the lower part, through linking means allowing said reversible operations between said above-mentioned active and retracted positions.

In this case, said linking means advantageously include means for the pivoting operation of said upper part with respect to said lower part, about at least one horizontal axis.

Preferably, the upper part is mounted at the end of two lateral uprights fastened to the lower part, which uprights are offset rearwardly with respect to the plane of the front wall of the lower part.

Still according to another characteristic, the front wall of the lower part has lateral edges that are continued, on the side of its rear face, by lateral returns made of a radioprotective material.

Preferably, these lateral returns each include an upper flap mobile about a vertical articulation formed along the lateral edge of the front wall of the lower part; and these upper flaps are mobile between a closed position in which they are located in or substantially in the plane of said lateral returns, and an open position in which they are adapted to be located in or substantially in the plane of the front wall of the lower part.

The lateral uprights of the screen are then advantageously arranged along the rear edge of the lateral returns of the lower part.

According to still another feature, the front wall of the upper part includes an upper panel made of a transparent radioprotective material that, once in active position, is inclined forwardly with respect to the front wall of the lower part, forming an overhanging, to allow the operator to move closer to the zone of intervention.

Preferably, the upper panel of the upper part is continued rearwardly by a covering panel made of a radioprotective material (preferably transparent).

On the other hand, the lateral edges of this upper panel, and possibly those of the covering panel, are continued rearwardly by lateral returns made of a radioprotective material.

Then, the lower end of the lateral returns of the upper part comprise a flexible curtain made of a radioprotective material, so as to create lateral passages for the operator's arms, in the continuation of the above-mentioned passage arranged between the front walls of the lower and upper parts of the screen.

Moreover, the lateral returns of the upper part of the screen each advantageously include a lower flap mobile about an articulation, which flaps carry said flexible curtains and are mobile between a closed position in which they are located in or substantially in the plane of said lateral returns, and an open position in which they are extended outwardly.

According to still another arrangement, the upper part of the screen is fastened to the lower part through lateral arms articulated about a first horizontal axis of articulation, forming a pivot, located at the upper end of the lateral uprights, which lateral arms are fastened to the lateral returns of said upper part, through a second horizontal axis of articulation, forming a pivot, located above said first axis of articulation, which articulations are associated with means for controlling the pivoting movements, such as cylinder(s) for example.

Preferably, the front wall of the lower part consists in a rigid panel made of a radioprotective material, in which is formed an opening closed by a flexible curtain in the form of a plurality of vertical strips of bands juxtaposed to each other, made of a radioprotective material, allowing the passage of devices or parts of devices though said opening.

On the other hand, the lower part of the screen is advantageously consisted of two complementary parts sliding vertically relative to each other, and which partially overlap each other to allow a variation of its height, which two parts are assembled to each other by means in the form of guides or slides associated with one or several actuators allowing to adapt the respective position of said two constitutive parts.

The invention also relates to an equipment in the form of a sterile cover intended to cover at least one part of the surface of a screen as defined herein above, such equipment comprising:

a flexible envelope adapted to come and cover the lower end of the front wall of the upper part and provided with means for the fixation thereof to said front wall, two flexible envelopes adapted to come and cover the mobile lower flaps of the lateral returns of the upper part, provided with means for the fixation thereof to said associated mobile flap, a flexible envelope adapted to come and cover the upper end of the front wall of the lower part and the upper flaps of the associated lateral returns, provided with means for the fixation thereof to said front wall and said flaps, and two structures for covering the lateral uprights, provided with means for the fixation thereof to said lateral uprights.

BRIEF DESCRIPTION OF THE DRAWING FIGURES

Other characteristics and advantages will appear from the reading of the following description of a particular embodiment, given only by way of example and shown in the appended drawings in which.

DETAILED DESCRIPTION OF THE INVENTION

The radioprotective screen 1 shown in FIGS. 1 to 6 comprises a lower part 2 and an upper part 3, which are mobile relative to each other, herein by rotation/pivoting of the upper part 3 with respect to the lower part 2, so as to allow the conformation thereof according to different configurations that will be detailed hereinafter.

The lower part 2 includes a base or stand 4, provided with wheels 5a, 5b for resting on the ground, from which extends upwardly a front wall 6 made of a radioprotective material (for example, for a part, a 2 mm lead equivalent massive steel, and for another part, a flexible plastic material charged with radio-attenuating metal particles), continued rearwardly by two lateral returns 7 also made of a radioprotective material (for example, a 1 mm lead equivalent massive steel).

The front wall 6 and the lateral returns 7 extend in a vertical or substantially vertical plane; they form together a structure with a U-shaped horizontal cross-section.

The front wall 6 is delimited by an upper edge 8, two lateral edges 9, a front face 10 and a rear face 11.

The upper edge 8 is horizontal and the lateral edges 9 are vertical.

In an alternative embodiment, the plane of this front wall 6 may be slightly inclined forwardly or rearwardly with respect to the vertical.

The two lateral returns 7 extend from lateral edges 9 of the front wall 6, rearwardly, i.e. on the side of the rear face 11 of this front wall 6, and straightly or, herein, in a slightly outwardly flared manner.

They each have—an upper edge 12 that continues rearwardly the horizontal upper edge 8 of the front wall 6, —a front edge 13 connected to one of the lateral edges 9 of the front wall 6, —a rear edge 14, —a front face 15 (directed the outside of the screen), and—a rear face 16 (directed to the inside of the screen).

These returns 7 each have an upper flap 7a that is mobile about a vertical articulation 7b formed on the lateral edge 9 opposite the front wall 6; each mobile flap 7a extends over a part of the height of the returns 7 (for example about half this height) and over all or part of their width. Their upper edge defines the upper edge 12 of the returns 7.

Hence, these mobile flaps 7a can occupy a closed position, as illustrated in FIGS. 1 to 6, in which they are located in the plane of the remaining of the returns 7; they are then locked in position by any suitable means, for example a removable latch, a magnet, and/or using ratchet hinges at their articulation to the ends of the front wall 6.

Figure 7:
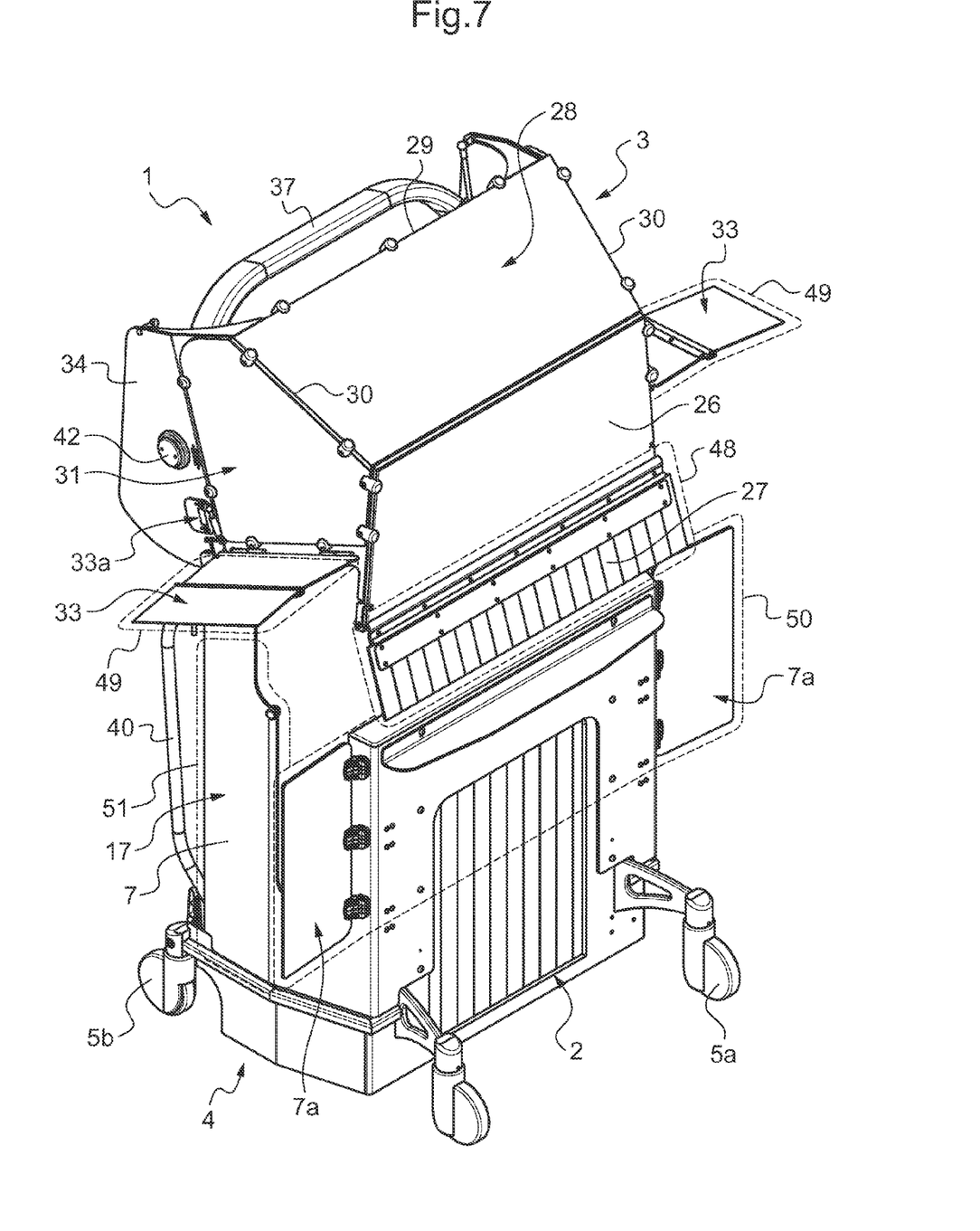
FIG. 7 is a view of the screen with its upper part in a partially retracted position, and with its lateral flaps in the open position, illustrating the installation of an equipment in the form of a sterile cover.

These mobile flaps 7a may also occupy an open position, in or substantially in the plane of the front wall 6, as illustrated in FIG. 7; then, their upper edge 12 is located in the alignment of the upper edge 8 of the front wall 6.

The base 4 of the screen 1 includes—two front wheels 5a that extend from the front face 10 of the front wall 6, on the sides and within the spatial requirement of the latter, and—two rear wheels 5b that extend in the continuation of the lateral returns 7.

Two lateral uprights 17 extend vertically along the rear edges 14 of the lateral returns 7.

These uprights 17 may be an integral part of the lateral returns 7, or may consist in independent added elements. They are offset rearwardly with respect to the plane of the front wall 6 and their upper end 19 extends above the level of the upper edges 12 of the lateral returns 7 and of the upper edge 8 of the front wall 6.

The upper part 3 of the screen 1 consists in a cap or caisson pivotally mounted on the lower part 2, and more particularly at the upper end 19 of the lateral uprights 17.

This upper part 3 has a front wall 20 made of a radioprotective material, delimited by an upper edge 21, a lower edge 22 and two lateral edges 23. It also has a front face 24 and a rear face 25.

This front wall 20 of the upper part 3 includes an upper panel 26 made of a transparent radioprotective material (for example, 2 mm lead equivalent laminated lead glass), of generally rectangular shape, continued downwardly by a flexible curtain 27, formed of a plurality of vertical strips or bands juxtaposed to each other, made of a radioprotective material (for example, a flexible plastic material including a radio-attenuating metallic filler).

This flexible curtain 27 extends over all the width of the upper panel 26; its upper end is fixed on the lower edge 26a of this panel 26, by any suitable means; its lower end is free.

As will be seen hereinafter, this flexible curtain 27 is intended to constitute a passage for the operator's arms (when the screen is in an active radioprotection configuration), and its height can be comprised between 20 and 30 cm, for example.

The lower edge 27a of the flexible curtain 27 constitutes the lower edge 22 of the front wall 20 of the upper part 3 of the screen 1; this lower edge 27a-22 is free.

The upper edge 26b of the upper panel 26 constitutes the upper edge 21 of the front wall 20; herein, this upper edge 26b is continued upwardly and rearwardly by a covering panel 28 also made of a preferably transparent radioprotective material (for example, a 0.5 mm lead equivalent lead-filled composite).

This covering panel 28 includes a rear free edge 29 and two lateral edges 30.

These lateral edges 30 extend in the continuation of the lateral edges 23 of the upper panel 26.

The upper panel 26 and the covering panel 28 are arranged in planes that form between each other an angle of the order of 120°.

The lateral edges 23 and 30 of the upper panel 26 and of the covering panel 28 are continued on the sides by lateral returns 31 made of a radioprotective material.

These returns 31 can extend perpendicular or substantially perpendicular to the plane of the panels 26 and 28, and hence parallel or substantially parallel to each other; in this case, they herein extend rearwardly in a slightly flared manner relative to each other.

The distance that separate them corresponds approximately to the distance that separates the lateral returns 7 of the lower part 2.

Each return 31 is in fact consisted by an upper panel 32 made of a preferably transparent radioprotective material (for example, a 0.5 mm lead equivalent lead-filled composite)—the front edge 32a of which is connected to the lateral edges of the upper 26 and covering 28 panels, —the lower edge 32b of which, which extends parallel or substantially parallel to the lower edge 26a of the panel 26 and which is arranged slightly above the latter, is continued downwardly by a flap 33 made of a radioprotective material, and—the rear edge 32c of which is continued by a platen 34, also made of a radioprotective material (for example, 1 mm lead equivalent massive steel).

The flaps 33 are pivotally mounted about the edge 32b that connects them to the upper panel 32, by means of hinges. They are consisted of a plate/base 35 made of a radioprotective material (for example, 0.75 mm lead equivalent massive steel), continued downwardly by a flexible curtain 36 also made of a radioprotective material (for example, flexible plastic material including a radio-attenuating metallic filler). The lower edge of the plate/base 35 extends at the lower edge 26a of the upper panel 26. The two flexible curtains 36 continue, on the sides, the flexible curtain 27 of the front wall 20.

When the flaps 33 are placed in the plane of their upper support panel 32, the flexible curtains 36 are positioned in the continuity of the front flexible curtain 27 and they extend rearwardly, straightly or in a slightly outwardly flared manner.

The height of the flexible curtains 36 correspond to that of the front flexible curtain 27.

Figure 4:
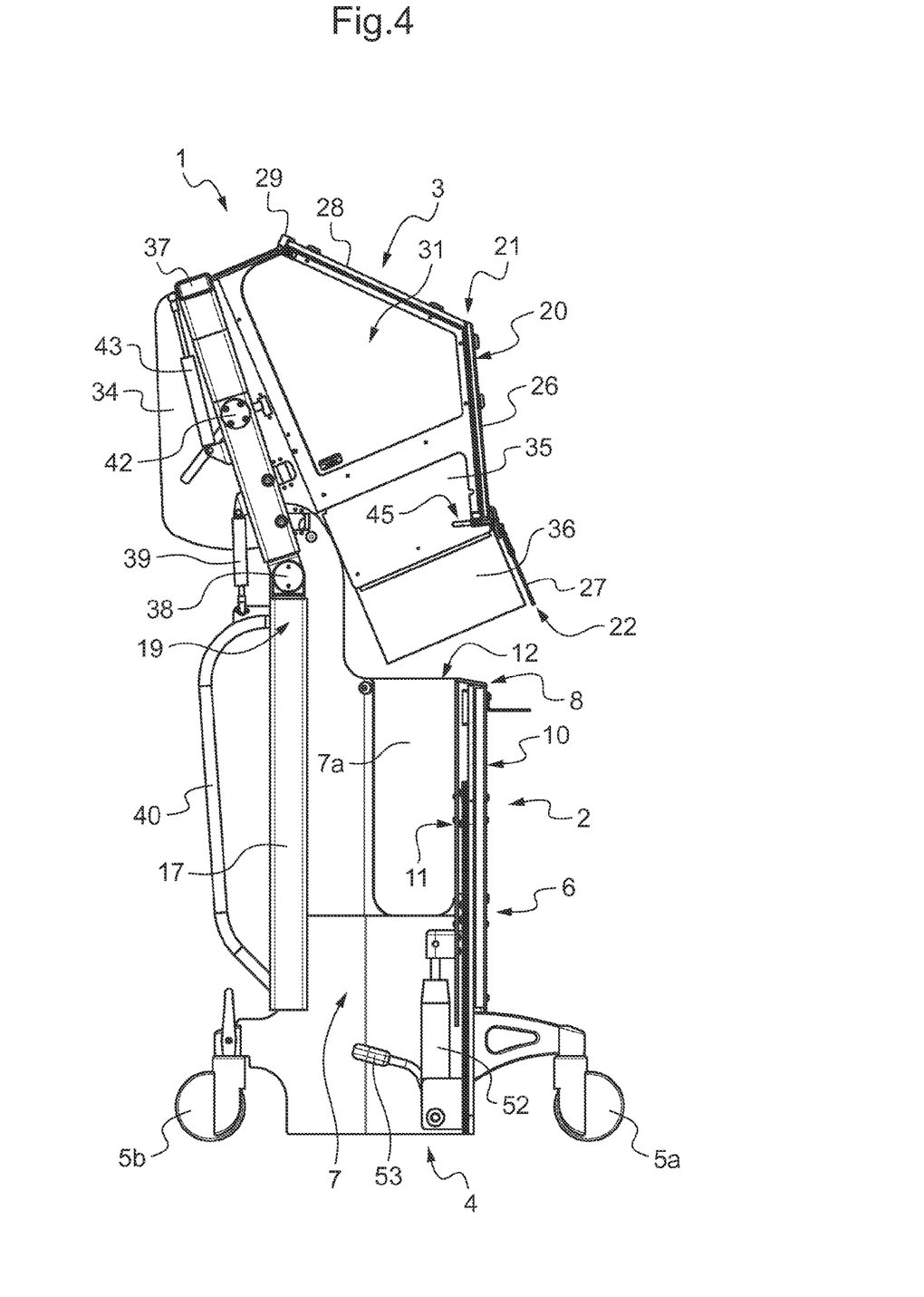
FIG. 4 is a vertical sectional view of the screen of FIG. 3.
Figure 5:
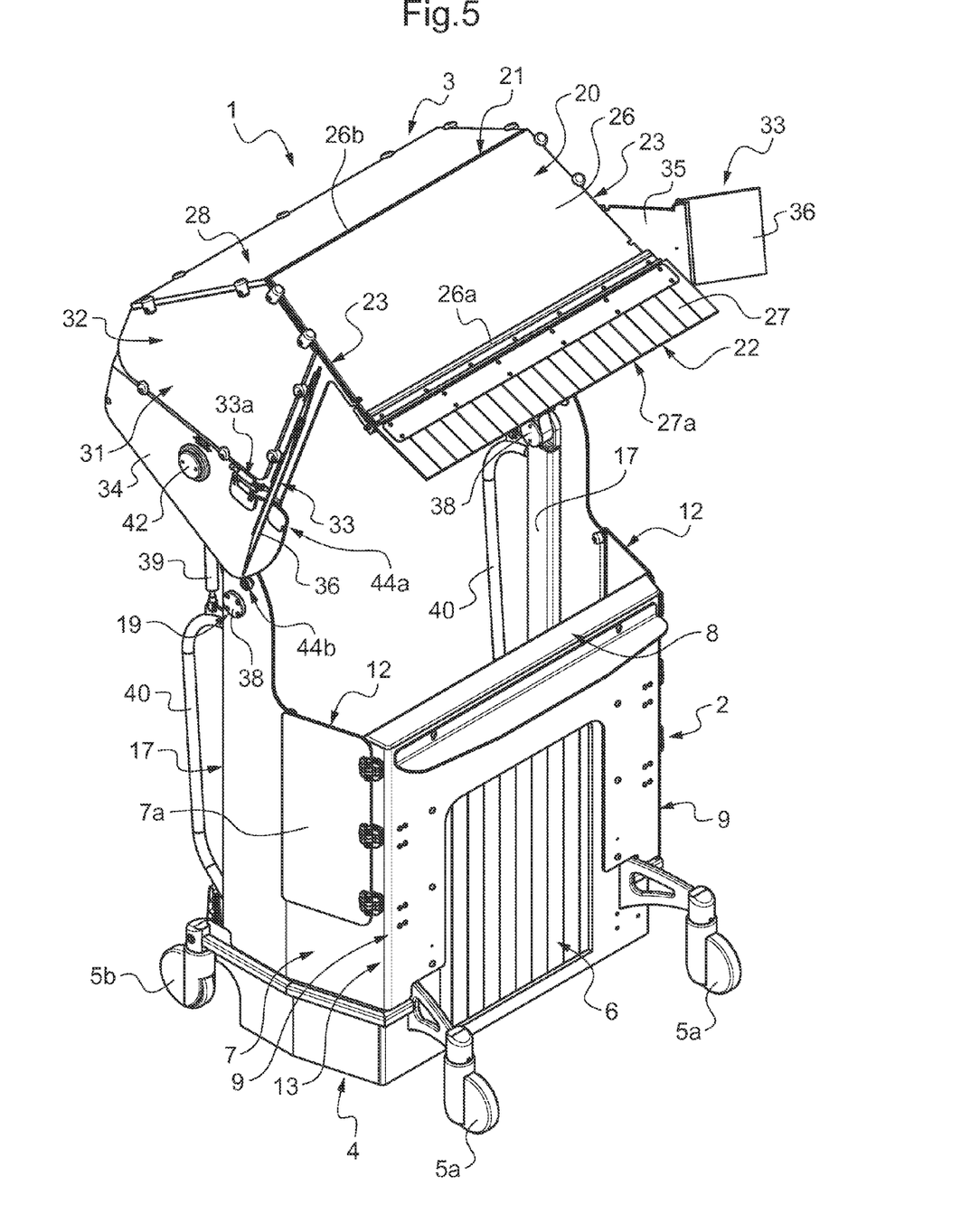
FIG. 5 is still a view of the same radioprotective screen, with its upper part in the fully retracted position.
Figure 6:
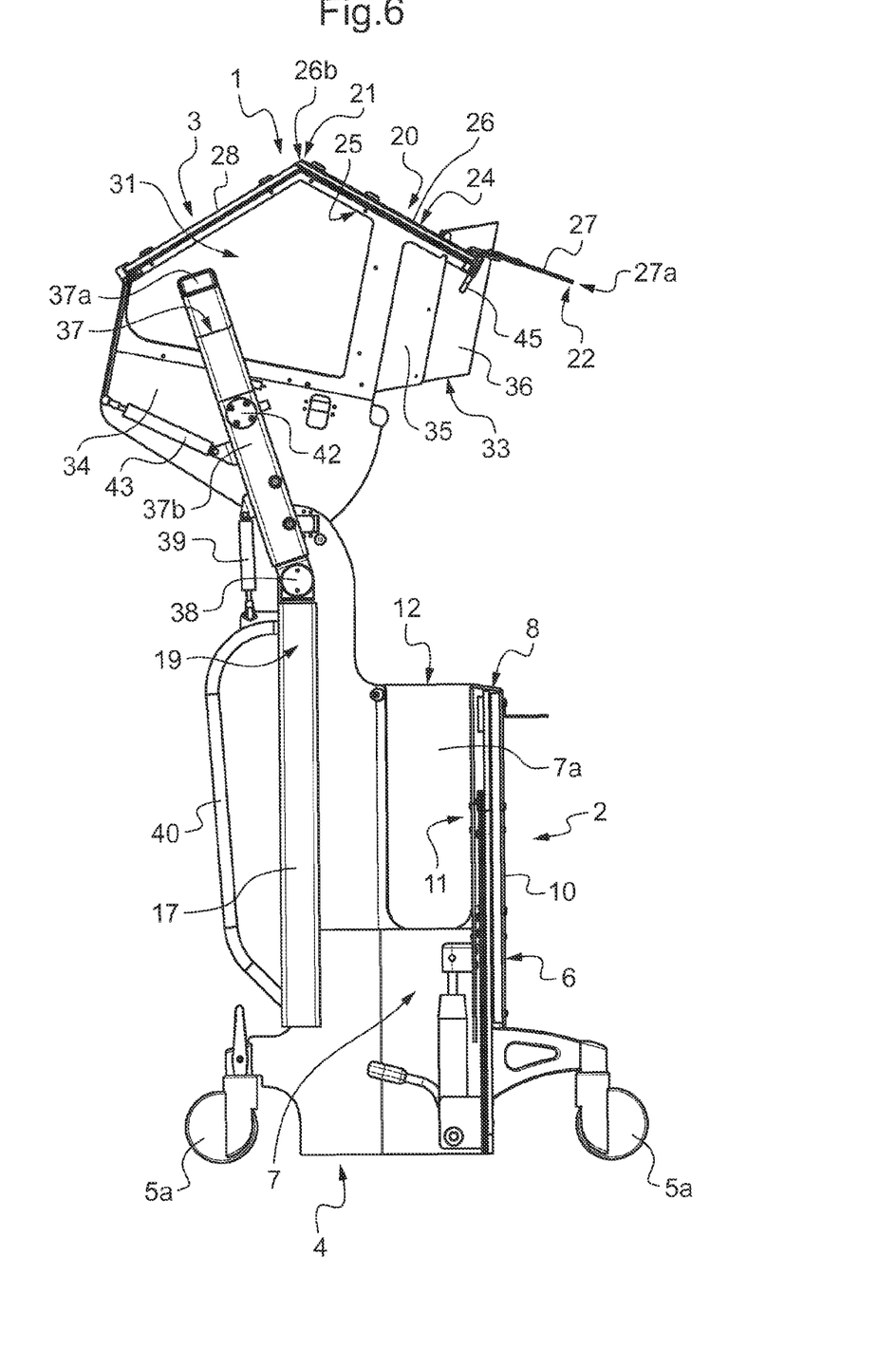
FIG. 6 is a vertical sectional view of the screen of FIG. 5.

The two lateral flaps 33 are pivotally mobile about the hinge formed on the above-mentioned edge 32b, between a closed position, in which they are located in the plane of the upper panels 32 (FIGS. 1 to 4) and an open position wherein they are outwardly spaced apart (FIGS. 5 to 7).

Their operation can be performed manually and/or automatically by a system of cable(s) associated with the pivoting of the upper part 3 of the screen, as detailed hereinafter. The corresponding articulation is associated with means for controlling the movement, consisted of a cylinder 33a, for example of the gas cylinder type, interposed between the plate/base 35 and the juxtaposed platen 34. The cylinder 33a has for function to maintain the flap 33 in the desired position, in particular for the installation of sterile covers.

The two platens 34 are connected by a carrier bow 37 formed of an upper crossbar 37a whose ends are continued rearwardly by two lateral arms 37b.

The crossbar 37a extends horizontally, approximately in the plane of the upper end of the lateral returns 31 and offset rearwardly with respect to the rear edge 29 of the covering panel 28.

The lower end of the arms 37b is assembled to the upper end 19 of the lateral uprights 17 of the lower part 2 of the screen through a first horizontal axis of articulation 38, forming a pivot, whose pivoting movement is controlled by two lateral cylinders 39, for example of the gas cylinder type.

Each of the cylinders 39 is interposed between a first fork joint fixed to one of the lateral arms 37b and a second fork joint fixed to the corresponding lateral upright 17 (herein, this second fork joint is carried by the upper end of one bow 40 adapted for operating the screen and each upright 17 is equipped with).

The ends of stroke of the two cylinders 39 define the rotational degree of freedom of the upper part 3 with respect to the lower part 2, about the axis 38; and these two cylinders 39 allow to damp the corresponding movement, in the two directions.

On the other hand, the lateral arms 37b are fastened to the lateral returns 31 (and in particular the platens 34 thereof) through a second horizontal axis of articulation 42, forming a pivot, whose movement is controlled by two lateral cylinders 43, for example also of the gas cylinder type.

Each of these cylinders 43 is interposed between a first fork joint fixed on one of the lateral arms 37b and a second fork joint fixed on the corresponding platen 34.

The ends of stroke of the two cylinders 43 define the rotational degree of freedom of the upper part 3 with respect to the bow 37 (and hence also with respect to the lower part 2), about the axis 42. These two cylinders 43 allow to damp the corresponding movement, in the two directions.

Preferably, the pivoting operation about the axis 42 is made possible only when the bow 37 is in maximum rearward tilting with respect to the lateral uprights 17, this by a system of locking stops 44a, 44b; in the other direction, the return to the closed position is firstly performed by the tilting about the axis 42, then about the axis 38, still thanks to the system of locking stops 44a, 44b.

The tilting movement about the axes 38 and 42 is obtained by a manual operation by the operator on the upper part 3, by means of operating handles 45 provided at the lower edge of the upper panel 26, on the rear face side of the latter, to be accessible from the inside of the screen 1.

Such a structure allows a mobility of the upper part 3 with respect to the lower part 2 of the screen, by pivoting about the above-mentioned pivot joints 38 and 42.

Figure 1:
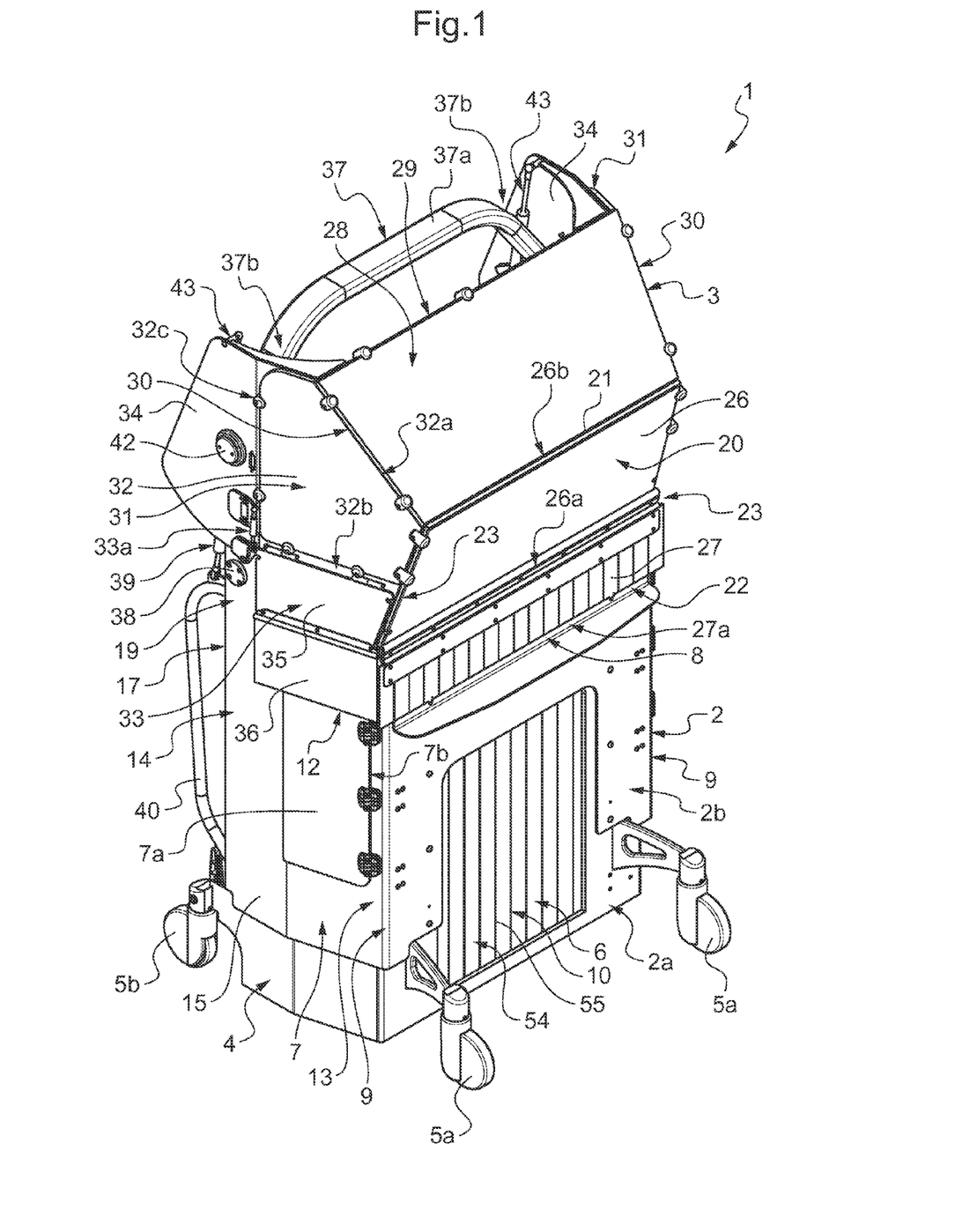
FIG. 1 shows a radioprotective screen according to the invention, in a ¾ front perspective view, and in the active radioprotection position.
Figure 2:
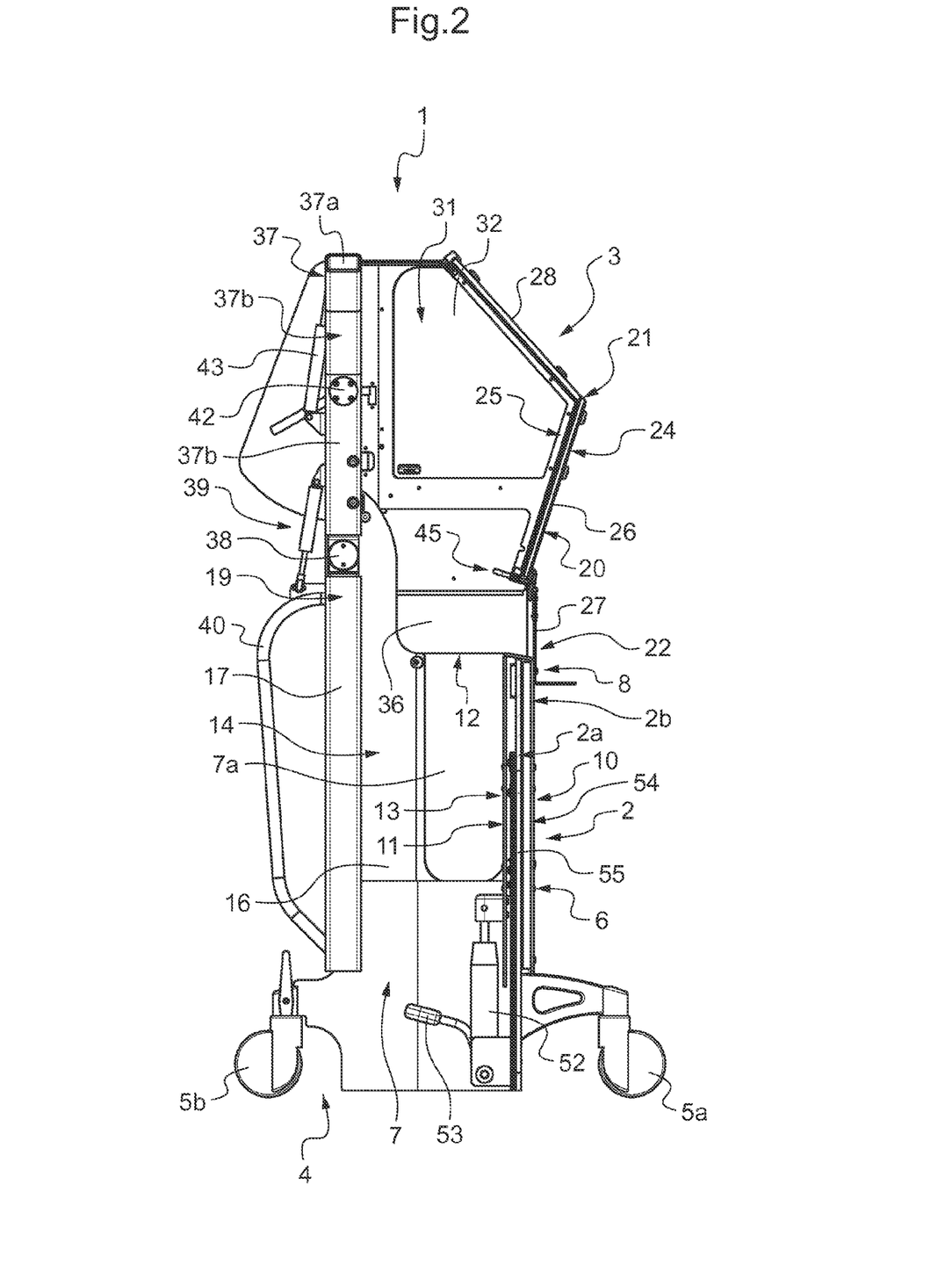
FIG. 2 is a vertical sectional view of the screen of FIG. 1.
Figure 3:
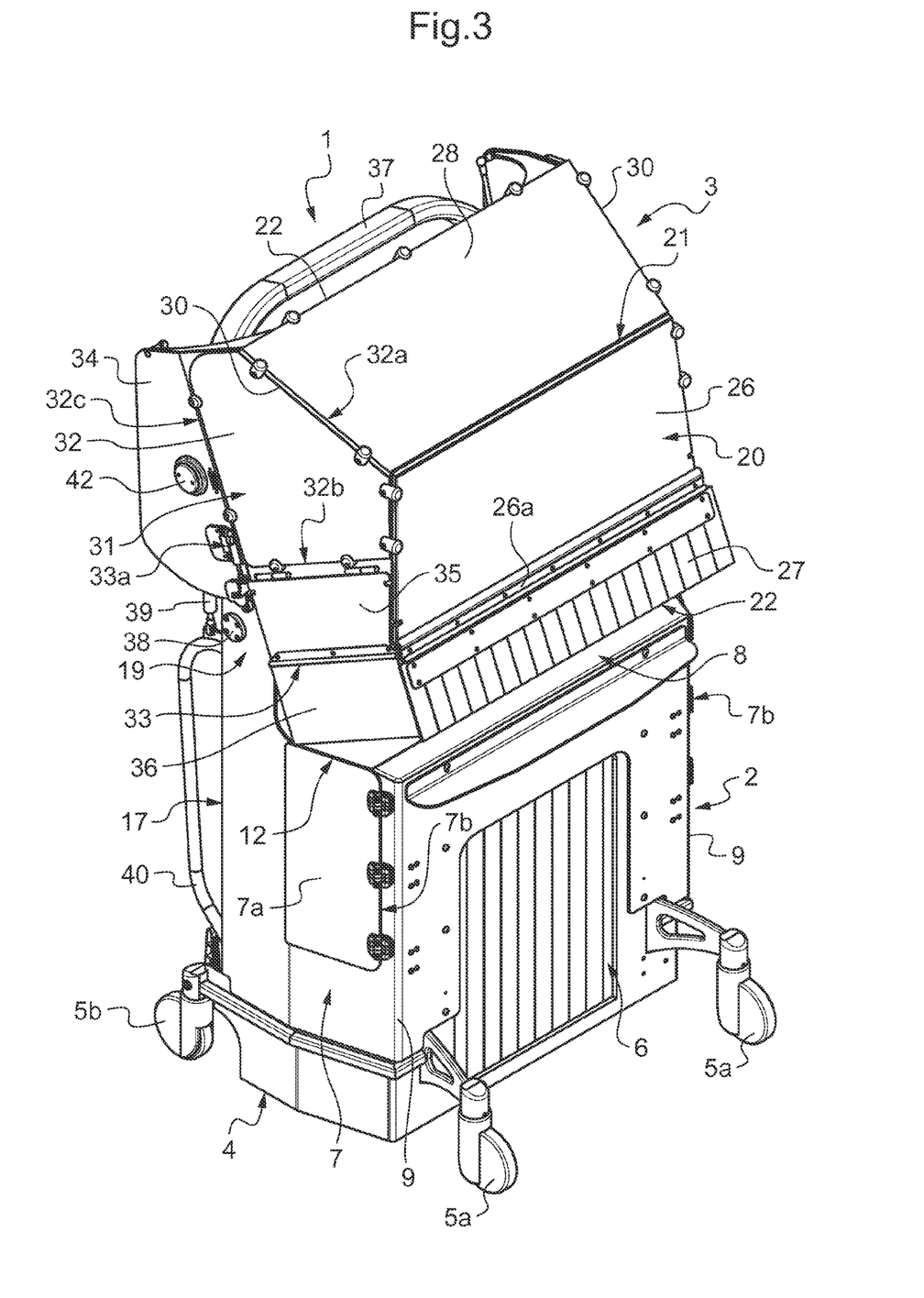
FIG. 3 shows the screen of FIGS. 1 and 2, in a ¾ front perspective view, but here with its upper part in a partially retracted position.

The front walls 20 and 6 of the upper 3 and lower 2 parts, as well as the lateral returns 31 and 7 that are associated therewith are hence reversibly separable from each other, and it is possible to conform the screen according to different configurations, in particular:

a so-called "active" configuration, illustrated in FIGS. 1 and 2, in which the upper part 3 is lowered forwardly toward the lower part 2, in such a manner that their front walls 6 and 20 come into the continuation of each other (like their associated returns 7 and 31) to ensure an efficient protection from the ionising radiations, a so-called partially "retracted" configuration, illustrated in FIGS. 3 and 4, in which the upper part 3 is tilted upwardly and slightly rearwardly by a pivoting movement about the axis 38, so as to separate said lower 6 and upper 20 front walls, with their associated returns, and hence clear a small space above the lower part 3, and a so-called "fully retracted" configuration, illustrated in FIGS. 5 and 6, in which the upper part 3 is possibly slightly upwardly tilted but also widely rearwardly tilted by a complementary pivoting movement about the axis 42, offering to the operator a significant freedom of movement above the lower part 3, for example toward a patient lying in front of the screen;

the corresponding cleared space is frontal and also lateral, due to the rearward offset of the lateral uprights 17 that carry the upper part 3 of the screen.

Advantageously, a cable control system ensures the outward spacing of the two flaps 33 during the pivoting of the upper part 3 rearwardly about the upper horizontal axis 42. This feature allows to clear even more the space for the operator, in particular on the sides, as illustrated in FIGS. 5 and 6.

The corresponding cables, not visible in the figures, suitably connect the arms 37b of the bow 37 and the plates/bases 35, by passing through suitable deflecting structures.

The rotation axis 42 extends above the axis 38; it is positioned approximately at half the height of the arms 37b.

The presence of these two rotation axes 38 and 42, offset in height, provides the upper part 3 with an optimum kinematics, during its rearward or forward tilting, by limiting its maximum level of elevation. This allows to limit the required space in height for the operation of the upper part 3 of the screen, for example to avoid the contact with devices or parts of devices located in height.

As an alternative, the upper part 3 of the screen may be articulated on the lateral uprights 17 about a single horizontal axis, in association with a suitable pivoting capacity.

According to still another alternative embodiment, it may also be contemplated to fasten the upper part 3 of the screen with the lateral uprights 17 through vertical slides, in association with one or several suitable actuators, to allow its vertical movement in height, to obtain the desired active and retracted positions.

In the active radioprotection position (FIGS. 1 and 2), the front wall 6 of the lower part 2 and the front wall 20 of the upper part 3 are arranged in the continuation of each other, like their lateral returns 7 and 31. The arms 37b are in the continuation of the lateral uprights 17.

The lower end 27a of the flexible curtain 27 arrives at the upper edge 8 of the front wall 6 of the lower part 2, or comes into slight overlap with the latter.

Likewise, the lower ends of the lateral flexible curtains 33 arrive at the upper edge 12 of the lateral returns 7 of the lower part 2, or come into slight overlap with these latter.

The flexible curtains 27 and 33 made of a radioprotective material, present at the zone of juxtaposition between lower 2 and upper 3 parts hence ensure a passage for the operator's arms, who will be able to accede to the patient and/or to devices present just in front of the screen, while remaining efficiently protected from the radiations.

This arm passage has a U-shaped horizontal cross-section, without discontinuity between the front face and the sides, which ensures an optimum comfort of intervention for the operator.

Its height, for example of the order of 20 to 30 cm, is adapted to optimize this comfort, while being minimized in such a manner to maintain an efficient radioprotection.

The corresponding arm passage is herein arranged at the lower edge of the upper front wall 20 and of its lateral returns 31; the flexible curtains 27 and 36 extend vertically by simple effect of gravity.

In an alternative embodiment, these flexible curtains can be provided at the upper edge of the front wall and the lateral returns of the lower part of the screen; these flexible curtains will then be maintained in vertical position by any suitable means.

As can be seen in FIG. 1, in this active radioprotection position, the upper panel 26, made of a transparent radioprotective material is inclined forwardly with respect to the vertical front wall 6 of the lower part 2 of the screen. This transparent panel 26 hence forms an overhanging and allows the operator to move closer to the zone of intervention located in front of the screen.

The corresponding overhanging angle is advantageously comprised between 10 and 30° with respect to the vertical (it is preferably of the order of 15 to 20° with respect to the vertical).

In this active radioprotection position, the rod of the cylinders 39 is in abutment in one of its stable positions, herein the maximum extraction.

When the operator wants it, for example at the beginning of the intervention, before the implementation of the means for generating ionising radiations, or during the intervention, for example to accede directly to the patient, he/she can lift the upper part 3 of the screen as illustrated in FIGS. 5 and 6, so as to create a frontal access opening, above the upper edges 8 and 12 of the lower part 2.

For that purpose, starting from the active position illustrated in FIGS. 1 and 2, the operator begins to tilt the upper part 3 upwardly, by gripping the operating handles 45.

The upper part 3 then pivots about the horizontal articulation 38, under the control of cylinders 39, to obtain the intermediate retracted position illustrated in FIGS. 3 and 4.

The rod of the cylinders 39 reaches its other stable position (retracted position), the corresponding pivoting may be of the order of 18°.

As explained hereinabove, during this first pivoting about the axis 38, the articulation about the axis 42 is locked by the system of locking stops 44a, 44b.

Once this first intermediate position reached, the suitable set of locking stops 44a, 44b releases the axes 42, and an additional thrust applied upwardly by the operator on the operating handles 45 leads to the pivoting of the upper part 3 about this axis 42.

This pivoting is performed under the control of the cylinders 43, until they reach their second stable position, herein with their rod fully retracted.

The fully retracted position illustrated in FIGS. 5 and 6 is then obtained.

This second pivoting can be made over an angular sector of the order of 60°, to obtain in total (i.e. with the pivoting about the axis 38) a pivoting of the order of 78°.

As stated hereinabove, the upward and rearward pivoting movement about the axis 42 is advantageously accompanied by the outward spacing of the flaps 33 (as can be seen in FIGS. 5 and 6), for example over an angular sector of the order of 40 to 60°, thanks to a suitable set of cables.

When the operator wants to come back to the active radioprotection position, he/she pulls on the operating handles 45 to begin lowering the upper part 3, by pivoting about the articulation axis 42, until the cylinders 43 reach their stable position with their rod fully extracted. Then, a continuation of the pulling operation leads to the second pivoting about the axis 38, under the control of the cylinders 39, until the rod of these latter arrive in its stable extracted position, to obtain the active configuration of the screen illustrated in FIGS. 1 and 2.

It is then understood that it is possible to obtain the active radioprotection and fully retracted positions in simple and rapid manner.

Within the framework of the use of the screen 1 in a sterile environment (for example for a surgical intervention), it is intended to cover at least one part of its different constitutive faces, and the screen is structured so as to allow a simple and rapid installation of this cover system.

In the present case, an equipment formed of a plurality of independent sterile elements is used to constitute this covering case. And the installation, as well as the removal of some of these elements, are performed in association with the pivoting of the above-mentioned flaps 7a and 33, as illustrated in FIG. 7.

As can be seen in FIG. 7, the installation of this sterile equipment is performed whereas the screen is in the intermediate retracted position (i.e., with its upper part 3 pivoted rearwardly about the axis 38 only).

Moreover, for that purpose, the flaps 33 of the returns 31 are manually spaced apart toward the outside (positioned, for example, straight with respect to the upper panel 32, and they are maintained in this position by the action of the associated cylinders 33a; moreover, the lower flaps 7a of the returns 7 are open and placed in or substantially in the plane of the front wall 6.

As illustrated in dashed line in FIG. 7, the sterile equipment used to ensure the protection of the screen 1 comprises several elements, including:

a flexible envelope 48, adapted to come and cover the lower end of the front wall 20 of the upper part 3. This flexible envelope 48 consists in two parallel panels, assembled on three of their edges and provided with an opening for its positioning about the flexible curtain 27 and the lower part of the transparent panel 26.

This flexible envelope 48 can be made of any suitable material, preferably transparent; its positioning opening may be lined by elastic means to facilitate its installation; it is also advantageously provided with means for the fixation thereof to the screen, for example an adhesive and/or suction pad system.

two flexible envelopes 49, adapted to come and cover the mobile lower flaps 33 of the lateral returns 31 of the upper part 3.

Each of these envelopes 49 is formed of two rectangular flaps fastened on three of their edges, the fourth edge constituting a positioning opening, advantageously associated with elastic means.

Each of these envelopes 49 is made of any suitable material, for example non transparent. Their opening may be lined by elastic means to facilitate their positioning; and each of these flexible envelopes 49 is provided with means for the fixation thereof to the associated flap 33, for example adhesive or suction pad means.

a flexible envelope 50 adapted to come and cover the upper end of the front wall 6 of the lower part 2 and the upper flaps 7a of the lateral returns 7.

Here again, this flexible envelope 50 is consisted of two rectangular flaps assembled at three of their edges, and the fourth edge of which constitutes a positioning opening. It is made of any suitable material, for example transparent, and comprises means for the fixation thereof to the screen, for example of the adhesive or suction pad type.

Its opening may be lined by elastic means to facilitate its positioning.

two structures 51 for covering the lateral uprights 17 (with possibly a part of the returns 7). Each of these structures 51 can be constituted of a simple rectangular panel made of a suitable material (for example a nonwoven material), which is conformed so as to come and cover the periphery of the uprights 17 (with possibly a part of the returns 7) and which is maintained in place by any suitable fixation means, for example adhesive means.

Once the different elements 48 to 51 of the sterile equipment correctly positioned, the flaps 33 and 7a are manually replaced in the closed position.

The level of positioning in height of the upper edge 8 of the lower part 2 of the screen advantageously corresponds to the level where the operator's forearms rest, to optimize the comfort of use thereof.

The corresponding height with respect to the ground may be of the order of 110 to 130 cm.

The lower part 2 of the screen 1 is preferably made of two telescopic parts 2a and 2b to allow an adjustment of height of the screen, and also the positioning in height of the flexible curtains 27, 33 for the passage of the arms, in particular as a function of the operator's size.

The bottom part 2a is fastened to the base 4 and is assembled to the telescopic top part 2b by means of suitable guides or slides (not visible on the figures), associated with operating means in the form of actuator(s) 52.

Figure 8:
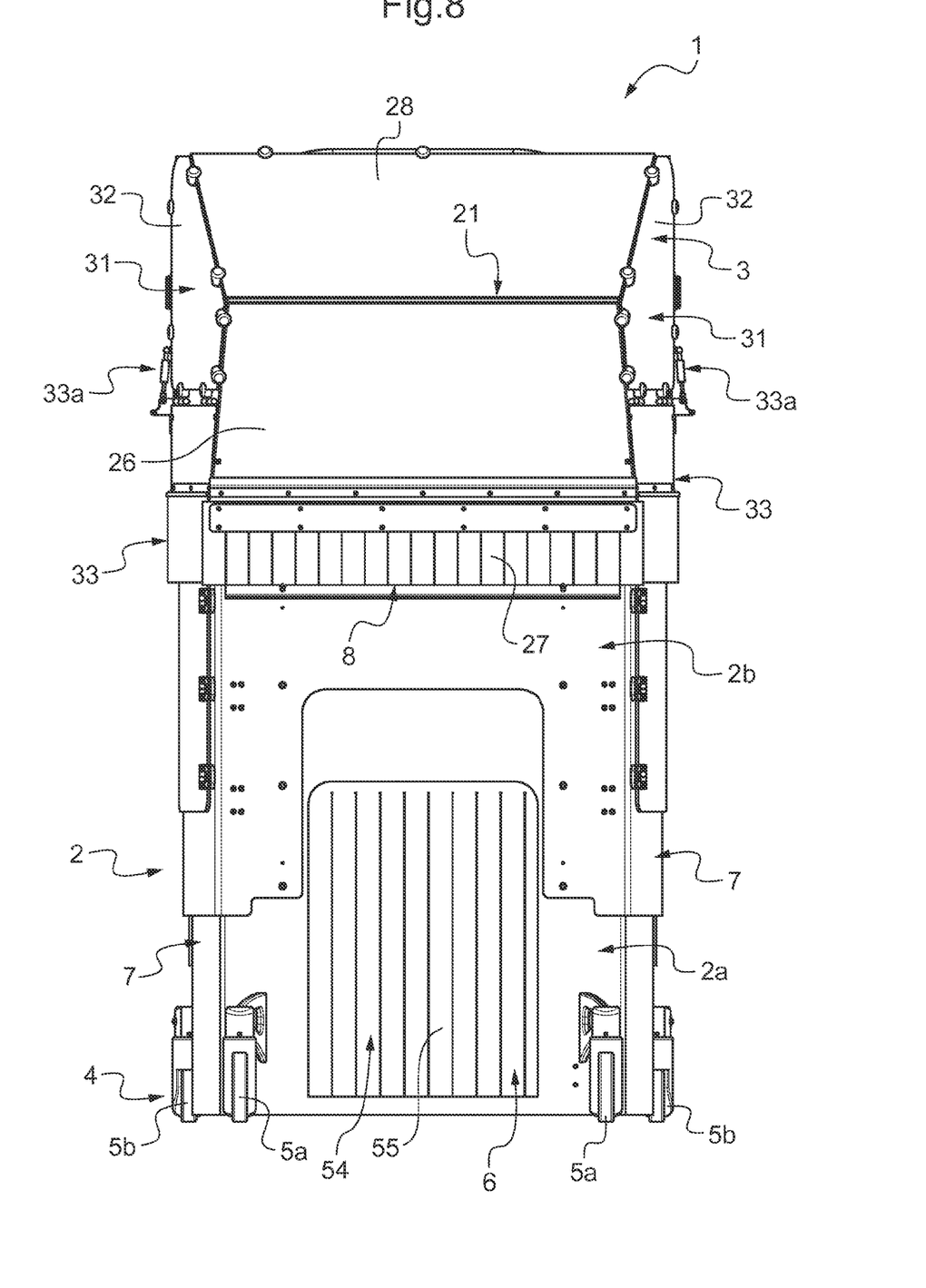
FIG. 8 is a face view of the screen according to FIGS. 1 to 7, herein in the active radioprotection position and with its lower part extended, to increase its height.

For example, an actuator 52 of the hydraulic cylinder type may be used, associated with a foot-operable control lever 53 (control pedal), adapted to manage a movement of lifting or lowering of the screen. FIGS. 1 to 7 illustrate the screen 1 in the low position, with its lower part 2 in the fully retracted position. FIG. 8 is a face view of the screen 1, illustrated herein in the high position with its extended lower part 2.

In FIGS. 1 to 8, it can be observed that the central zone of the front wall 6 of the lower part 2 includes an opening 54 closed by a flexible curtain 55 in the form of a plurality of vertical strips or bands juxtaposed to each other, made of a radioprotective material (for example, a plastic material filled with radio-attenuating metallic particles).

Such an opening 54 associated with a flexible curtain 55 allows the passage of devices or parts of devices through it (for example, the head of the X-ray emitting bow), while maintaining an efficient radioprotection.

For example, the opening 54 in question may be made in a rigid panel made of a radioprotective material constitutive of the bottom part 2a of the lower part 2, on the upper edge of which are fixed the flexible strips or bands made of radioprotective material; and the telescopic top part 2b of the lower part 2 then includes an opposite opening, adapted not to hamper the passage through said flexible curtain.

The invention claimed is:

1. A screen made of a radioprotective material for protecting an operator from the ionising radiations, comprising:
    (i) a lower part that has a base and at least one front wall made of a radioprotective material, said front wall extends in a vertical or substantially vertical plane and has an upper edge, a front face and a rear face,
    (ii) an upper part having at least one front wall made of a radioprotective material, at least one part of which is transparent to allow a visual access through said front wall, said front wall has a front face, a rear face and a lower edge, and
    (iii) at least one passage for the operator's arms,
    wherein said passage for the operator's arms is arranged at a level of the lower edge of the front wall of the upper part and comprises a flexible curtain comprising a plurality of vertical strips or bands juxtaposed to each other, made of a radioprotective material, and an upper end of said flexible curtain is fixed on an upper panel made of a radioprotective material, and a lower edge of the flexible curtain constitutes the lower edge of the front wall,
    said front wall of the lower part and said front wall of the upper part being arranged in a continuation of each other, by juxtaposition of their respective upper and lower edges, then occupying an active position ensuring the desired protection,
    wherein said front walls of the upper part and of the lower part are separable from each other, said upper part being carried by said lower part through linking means allowing the reversible operation thereof to a retracted position in which the lower edge of said front wall of said upper part is spaced apart from the upper edge of said front wall of said lower part, to clear a space above said lower part, and
    said linking means including means for the pivoting operation of said upper part with respect to said lower part, about at least one horizontal axis, the movements about said at least one horizontal axis being obtained by a manual operation by the operator by means of operation handles.

2. The screen according to claim 1, wherein the upper part is mounted at the end of two lateral uprights fastened to the lower part, which uprights are offset rearwardly with respect to the plane of the front wall of said lower part.

3. The screen according to claim 1, wherein said front wall of the lower part has lateral edges that are continued, on the side of its rear face, by lateral returns made of a radioprotective material.

4. The screen according to claim 3, wherein said lateral returns each have an upper flap mobile about a vertical articulation arranged along the lateral edge opposite of the front wall of the lower part, which upper flaps are mobile between a closed position in which they are located in or substantially in the plane of said lateral returns, and an open position in which they are adapted to be located in or substantially in the plane of said front wall of the lower part.

5. The screen according to claim 2, wherein said front wall of the lower part has lateral edges that are continued, on the side of its rear face, by lateral returns made of a radioprotective material, and said lateral uprights are arranged along the rear edge of the lateral returns of the lower part.

6. The screen according to claim 1, wherein the front wall of the upper part includes an upper panel made of a transparent radioprotective material that, once in active position, is inclined forwardly with respect to the front wall of the lower part, forming an overhanging, to allow the operator to move closer to the zone of intervention.

7. The screen according to claim 6, wherein said upper panel of the upper part is continued rearwardly by a covering panel made of a radioprotective material.

8. The screen according to claim 7, wherein the lateral edges of said upper panel, and those of said covering panel, are continued rearwardly by lateral returns made of a radioprotective material.

9. The screen according to claim 8, wherein the passage for the operator's arms is arranged at the level of the zone of juxtaposition between said lower and upper parts, when these latter are in an active juxtaposed position, and the lower end of the lateral returns of said upper part comprise a flexible curtain made of a radioprotective material, so as to create lateral passages for the operator's arms, in the continuation of said passage arranged between said front walls of the lower and upper parts.

10. The screen according to claim 8, wherein said lateral returns of said upper part each include a lower flap mobile about an articulation, which flaps include said flexible curtains and are mobile between a closed position in which they are located in or substantially in the plane of said lateral returns, and an open position in which they are extended outwardly.

11. The screen according to claim 8, wherein said upper part is carried by said lower part, through linking means allowing said reversible operations between said active position and said retracted position, said linking means including means for the pivoting operation of said upper part with respect to said lower part, about at least one horizontal axis, said upper part being mounted at the end of two lateral uprights fastened to the lower part, which uprights are offset rearwardly with respect to the plane of the front wall of said lower part, wherein the upper part is fastened to the lower part through lateral arms articulated about a first horizontal axis of articulation, forming a pivot, located at the upper end of the lateral uprights, which lateral arms are fastened to the lateral returns of said upper part, through a second horizontal axis of articulation, forming a pivot, located above said first axis of articulation, which articulations are associated with means for controlling the pivoting movements, of the cylinder type for example.

12. The screen according to claim 1, wherein the front wall of the lower part consists in a rigid panel made of a radioprotective material, in which is formed an opening closed by a flexible curtain in the form of a plurality of vertical strips of bands juxtaposed to each other, made of a radioprotective material, allowing the passage of devices or parts of devices though said opening.

13. The screen according to claim 1, wherein the lower part is consisted of two complementary parts sliding vertically relative to each other, and which partially overlap each other to allow a variation of its height, which two parts are assembled to each other by means in the form of guides or slides associated with one or several actuator(s) allowing to adapt the respective position of said two constitutive parts.

14. An equipment in the form of a sterile cover intended to cover at least one part of the height of a screen according to claim 10, wherein said front wall of the lower part has lateral edges that are continued, on the side of its rear face, by lateral returns made of a radioprotective material, and said lateral returns each have an upper flap mobile about a vertical articulation arranged along the lateral edge opposite of the front wall of the lower part, which upper flaps are mobile between a closed position in which they are located in or substantially in the plane of said lateral returns, and an open position in which they are adapted to be located in or substantially in the plane of said front wall of the lower part the equipment further comprising:
- a flexible envelope adapted to come and cover the lower end of the front wall of the upper part and provided with means for the fixation thereof to said front wall,
- two flexible envelopes adapted to come and cover the mobile lower flaps of the lateral returns of the upper part, provided with means for the fixation thereof to said associated mobile flap,
- a flexible envelope adapted to come and cover the upper end of the front wall of the lower part and the upper flaps of the associated lateral returns, provided with means for the fixation thereof to said front wall and said flaps, and
- two structures for covering the lateral uprights, with possibly a part of the returns, provided with means for the fixation thereof to said lateral uprights and possibly the returns.

* * * * *